US012691300B2

(12) United States Patent
Patel et al.

(10) Patent No.: US 12,691,300 B2
(45) Date of Patent: Jul. 28, 2026

(54) LASER SYSTEM AND METHODS FOR CUTANEOUS TREATMENTS AND SURGERY

(71) Applicant: Duke University, Durham, NC (US)

(72) Inventors: Jigar Patel, Durham, NC (US); Weston Ross, Durham, NC (US); Matthew Tucker, Durham, NC (US); Guangshen Ma, Durham, NC (US); Patrick Codd, Durham, NC (US)

(73) Assignee: Duke University, Durham, NC (US)

( * ) Notice: Subject to any disclaimer, the term of this patent is extended or adjusted under 35 U.S.C. 154(b) by 912 days.

(21) Appl. No.: 17/928,505

(22) PCT Filed: Jun. 18, 2021

(86) PCT No.: PCT/US2021/038108
§ 371 (c)(1),
(2) Date: Nov. 29, 2022

(87) PCT Pub. No.: WO2021/258003
PCT Pub. Date: Dec. 23, 2021

(65) Prior Publication Data
US 2023/0201627 A1 Jun. 29, 2023

Related U.S. Application Data

(60) Provisional application No. 63/041,155, filed on Jun. 19, 2020.

(51) Int. Cl.
*A61N 5/067* (2006.01)
*A61B 5/00* (2006.01)
(Continued)

(52) U.S. Cl.
CPC ........... *A61N 5/067* (2021.08); *A61N 5/0616* (2013.01)

(58) Field of Classification Search
CPC ...... A61B 18/20–18/28; A61N 5/06–2205/073
(Continued)

(56) References Cited

U.S. PATENT DOCUMENTS

RE37,504 E * 1/2002 Lin ...................... B23K 26/361
606/4
2002/0010500 A1 1/2002 Chen
(Continued)

OTHER PUBLICATIONS

Authorized Officer: Kari Rodriquez, International Search Report and Written Opinion issued in PCT application No. PCT/US2021/038108, Oct. 1, 2021, 10 pp.

*Primary Examiner* — Jonathan T Kuo
*Assistant Examiner* — Vynn V Huh
(74) *Attorney, Agent, or Firm* — Kaplan Breyer Schwarz, LLP

(57) ABSTRACT

A laser treatment system includes a sensor configured to detect a targeted therapy region. A processing unit is configured to generate a treatment path that consists of sequentially arranged laser spots to enable the treatment path to fully encompass a targeted therapy region to receive laser therapy. A steering device is alerted to move to a plurality of positions based on the treatment plan generated by the processing unit. A treatment laser provides laser therapy to the plurality of positions and targeted therapy region based on the treatment plan generated by the processing unit.

20 Claims, 7 Drawing Sheets 210   220

(51) Int. Cl.
    *A61B 17/00*       (2006.01)
    *A61B 18/00*       (2006.01)
    *A61B 90/00*       (2016.01)
    *A61N 5/06*       (2006.01)

(58) Field of Classification Search
    USPC ..................................... 606/2–19; 607/88–94
    See application file for complete search history.

(56)              References Cited

U.S. PATENT DOCUMENTS

| | | | |
|---|---|---|---|
| 2004/0059321 A1 | 3/2004 | Knopp et al. | |
| 2008/0015553 A1* | 1/2008 | Zacharias | A61F 9/008 |
| | | | 606/4 |
| 2011/0254948 A1* | 10/2011 | Eisfeld | G06V 20/69 |
| | | | 382/128 |
| 2013/0345683 A1* | 12/2013 | Mordaunt | A61F 9/00821 |
| | | | 606/4 |
| 2014/0257257 A1 | 9/2014 | Grant et al. | |
| 2016/0095660 A1* | 4/2016 | Choye | A61B 18/203 |
| | | | 606/9 |

* cited by examiner

LASER SYSTEM AND METHODS FOR CUTANEOUS TREATMENTS AND SURGERY

CROSS REFERENCE TO RELATED APPLICATIONS

This application claims the benefit of U.S. Provisional Application Ser. No. 63/041,155 filed Jun. 19, 2020, entitled "Laser System and Methods for Cutaneous Treatments and Surgery", which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING GRANT

This disclosure was made with a Grant from the American Society of Dermatologic Surgery.

FIELD OF THE TECHNOLOGY

The present disclosure relates to optimal treatment paths generated in laser treatment systems. More particularly, generating an optimal treatment path to treat targeted therapy regions in a laser treatment system.

BACKGROUND

Currently, laser-based devices and systems are being used across a wide range of cutaneous applications that include vascular and pigmented lesions, skin rejuvenation, and skin cancers among elective and non-elective procedures. Light-based devices are being used to treat conditions such as basal cell carcinoma (BCC), squamous cell carcinoma (SCC), and melanoma.

During the treatment of these various conditions, hand-guided lasers deliver laser therapy to a circumcised area defined by the shape of the laser spot. The hand-guided laser(s) is also sequentially repositioned to deliver treatment to the entire cancerous surgical site.

The geometric constraints imposed by the shape of the laser spot, which is often a fixed size square or circle, can make it difficult to deliver uniform therapy to only the targeted area. Moreover, collateral damage can occur to surrounding healthy skin around the laser spot. In some cases, the laser treatment far exceeds the boundaries of the targeted pigmented lesion.

Accordingly, a need exits for a laser treatment system to provide uniform laser therapy to a targeted therapy region. In addition, a need exists for the uniform laser therapy to be delivered to the targeted therapy region while minimizing collateral damage and pain to healthy skin and tissue surrounding the targeted therapy region.

SUMMARY

Embodiments of the present disclosure employ a process for providing laser therapy to a targeted tissue region using an optimal path generated by a processing unit with a computing device.

The processing unit within the computing device can be connected to a sensor such as, but not limited to, a depth camera and/or a color camera. The processing unit can also be connected to a steering mechanism that can be used to move a treatment laser to various positions and enable the treatment laser to provide laser therapy at various positions.

The processing unit generates an optimal path by using a series of patterns in which laser spots are positioned on a surface of a tissue region. The steering mechanism will move the treatment laser to a plurality of positions to enable the treatment laser to provide the laser spots on the surface of the tissue. As a result, a final pattern can be produced in which a targeted therapy region that encompasses a tumor region of the patient is identified. The processing unit can alert or provide a command to the treatment laser to provide laser therapy to the targeted therapy region.

An illustrative embodiment of the present disclosure is laser treatment system comprising a sensor configured at a first position configured to detect a targeted therapy region. The laser treatment system also includes a processing unit is connected to the sensor. Further, the processing unit is configured to generate a treatment path, wherein the treatment path consists of sequentially arranged laser spots to enable the treatment path to fully encompass a targeted therapy region to receive laser therapy. The laser treatment system also includes a steering device connected to the processing unit, and configured to move to a plurality of positions based on the treatment path generated by the processing unit. Further, the laser treatment system also includes a treatment laser connected to the steering device, and configured to provide the laser therapy to the plurality of positions and the targeted therapy region based on the treatment path generated by the processing unit.

In some embodiments, the sensor is a three-dimensional depth sensing camera or laser scanner that takes an image of the targeted therapy region.

In some embodiments, the treatment path includes a first pattern of laser spots that are each configured a set distance apart.

In some embodiments, the treatment path includes a second pattern of laser spots that are offset by another set distance from the first pattern of laser spots.

In some embodiments, the processing unit adjusts the treatment path to leave a negative surgical margin.

An illustrative embodiment of the present disclosure also includes a system of one or more sensors configured to take an initial image of a surgical site. The system also includes a processing unit connected to the one or more sensors. The processing unit is configured to generate a treatment path for a targeted tissue region to be treated at the surgical site based on the initial image of the surgical site by generating the treatment path to surround a targeted tissue region to ensure that the targeted tissue region receives laser therapy. The system also includes a steering device connected to the processing unit and the one or more sensors and configured to move to various positions at the surgical site based on the treatment path generated by the processing unit. The system also includes a treatment laser connected to the steering device and processing unit, wherein the treatment laser provides the laser therapy to the targeted tissue region based on the treatment path generated by the processing unit.

In some embodiments, the one or more sensors include dual stereovision cameras configured to take a final image of the surgical site.

In some embodiments, the treatment path includes a first pattern of laser spots and a second pattern of laser spots, and a third pattern that merges the first pattern and second pattern of laser spots.

In some embodiments, the processing unit adjusts an energy density enable the laser therapy to be provided to the targeted tissue region.

In some embodiments, the processing unit extends the laser therapy outside of the targeted tissue region.

In an embodiment of the present disclosure, a method includes establishing a sensor in a first position to detect a targeted therapy region. The method also includes positioning a processing unit in a second position to be connected to the sensor, wherein the processing unit is generating a treatment path, wherein the treatment path consists of sequentially arranged laser spots to enable the treatment path to fully encompass a targeted therapy region to receive laser therapy. The method also includes establishing a steering device to be connected to the processing unit, wherein the steering device is moving to a plurality of positions based on the treatment path generated by the processing unit. Further, the method includes positioning a treatment laser to be connected to the steering device and processing unit, wherein the treatment laser is providing the laser therapy to the plurality of positions and to the targeted therapy region based on the treatment path generated by the processing unit.

In some embodiments, the sensor is a laser distance sensor that is configured to take an initial image and a final image of the targeted therapy region.

In some embodiments, the treatment path includes a final pattern created for a first, second, and third pattern by removing laser spots that are not positioned within the targeted therapy region.

In some embodiments, the laser therapy is spatially varied across the targeted region.

In some embodiments, a portion of a targeted lesion area is not treated with the laser therapy.

DETAILED DESCRIPTION

The following disclosure can be performed for benign pigmented skin lesions (lentigos, seborrheic keratoses, etc.), as well as various patient cancer treatments. Moreover, the proposed treatment can provide uniform therapy to a targeted therapy region while minimizing collateral damage to surrounding healthy skin. Moreover, the laser-control technology on a laser treatment system 100 shown in FIG. 1(A) and FIG. 1(B) using computer-guided laser therapy with small laser spot sizes can overcome current problems in laser therapy.

Figure (FIG. 1(A) described below is not intended to limit the disclosure to a specific apparatus. A patient can require laser treatment. One or more tissue regions of the patient can be applied with the laser treatment using the laser treatment system 100. As the patient is positioned on an operating table, the laser treatment system 100 can use a series of patterns to identify a targeted tissue region of the patient that should be treated with laser therapy. The components of the laser treatment system 100 described below can assist a treatment laser within the laser treatment system 100 identifying the targeted tissue region of the patient, and with applying the laser treatment to the targeted tissue region. The application of computer-guided laser therapy can overcome current problems in laser therapy and improve patient care for the treatment of cutaneous diseases that are amenable to laser therapy.

Figure 1A:
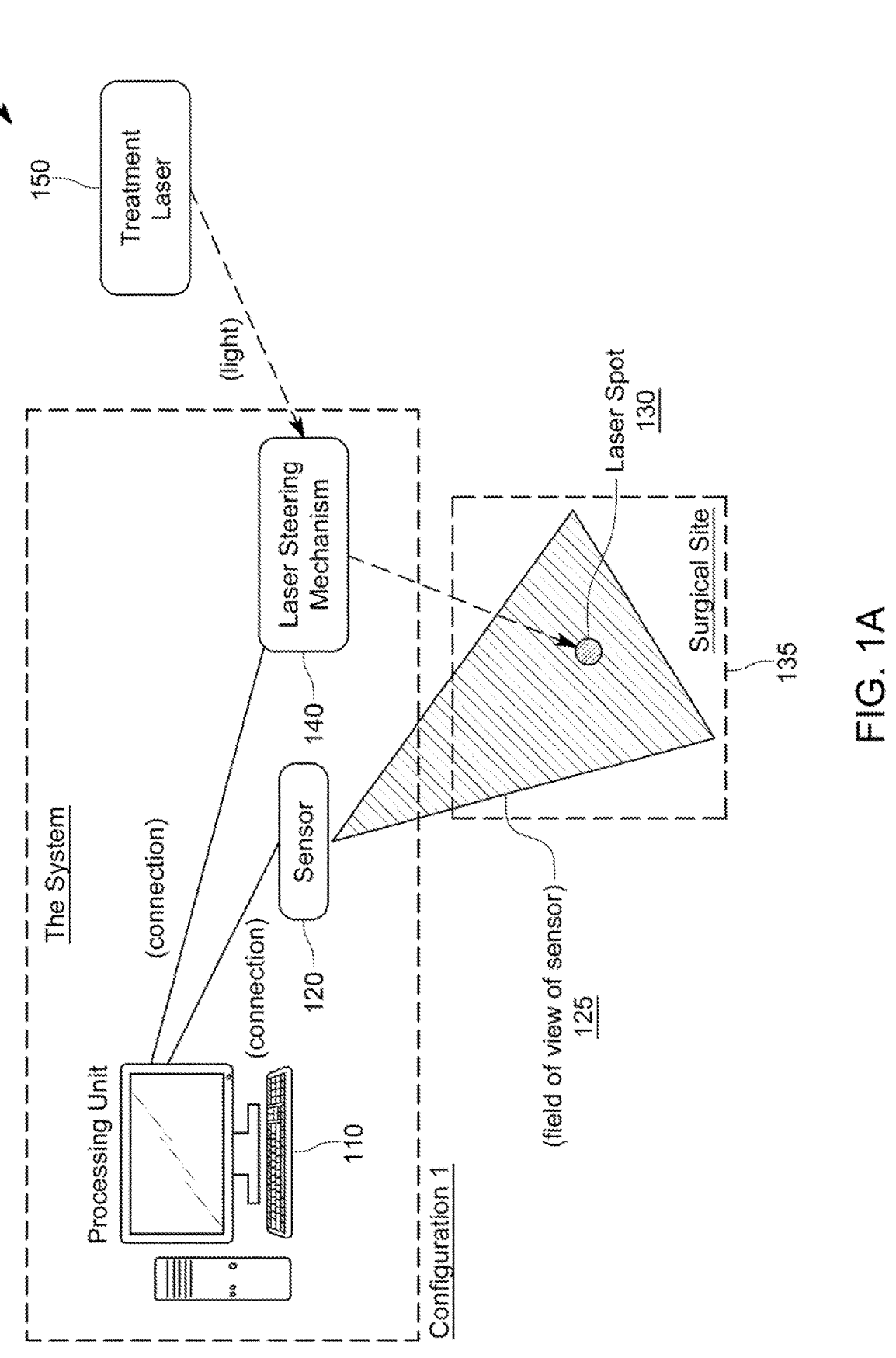
FIG. 1(A) depicts a block diagram of a laser treatment system in accordance with an illustrative embodiment of the present disclosure.

FIG. 1(A) depicts a block diagram of a laser guidance system 100. A processing unit 110 is configured within a computing device. An imaging sensor is connected to the processing unit 110. The sensor 120 is configured to take both initial and final images of the surgical site 135. The sensor 120 can use a field of view 125 that includes a laser spot 130. A laser steering mechanism 140 will be connected to the processing unit 110 and the sensor 120. The processing unit 110, sensor 120, and laser steering mechanism 140 are accessories to an existing treatment laser 150. The laser steering mechanism 140 is configured to move the treatment laser 150 to various positions based on an optimal treatment path which the processing unit 110 generates.

In FIG. 1(A), the processing unit 110 can generate an optimal treatment path to/for a targeted lesion and/or targeted therapy region. In FIG. 1(A), a laser spot 130 is illustrated. As will be described further in FIGS. 2(A) and 2(B), a plurality of laser spots 130 will be used to provide a series of patterns to enable a targeted therapy region to surround a targeted tumor or lesion to be treated with laser therapy. The optimal path can create a series of patterns to identify a targeted therapy region that encompasses a targeted lesion with in a patient. The optimal path will include a first pattern of laser spots 130 that are configured one diameter apart. The optimal path will also include a second pattern of laser spots 130 that are shifted in a lateral and longitudinal direction from the first pattern of laser spots 130 by a fixed diameter set by the processing unit 110. The optimal path will also include a third pattern that merges the first and second pattern of laser spots 130. The optimal path will further include a final pattern that is created from the third pattern by removing the laser spots 130 that do not overlap with the targeted therapy region that encompasses the targeted lesion of the patient.

Figure 1B:
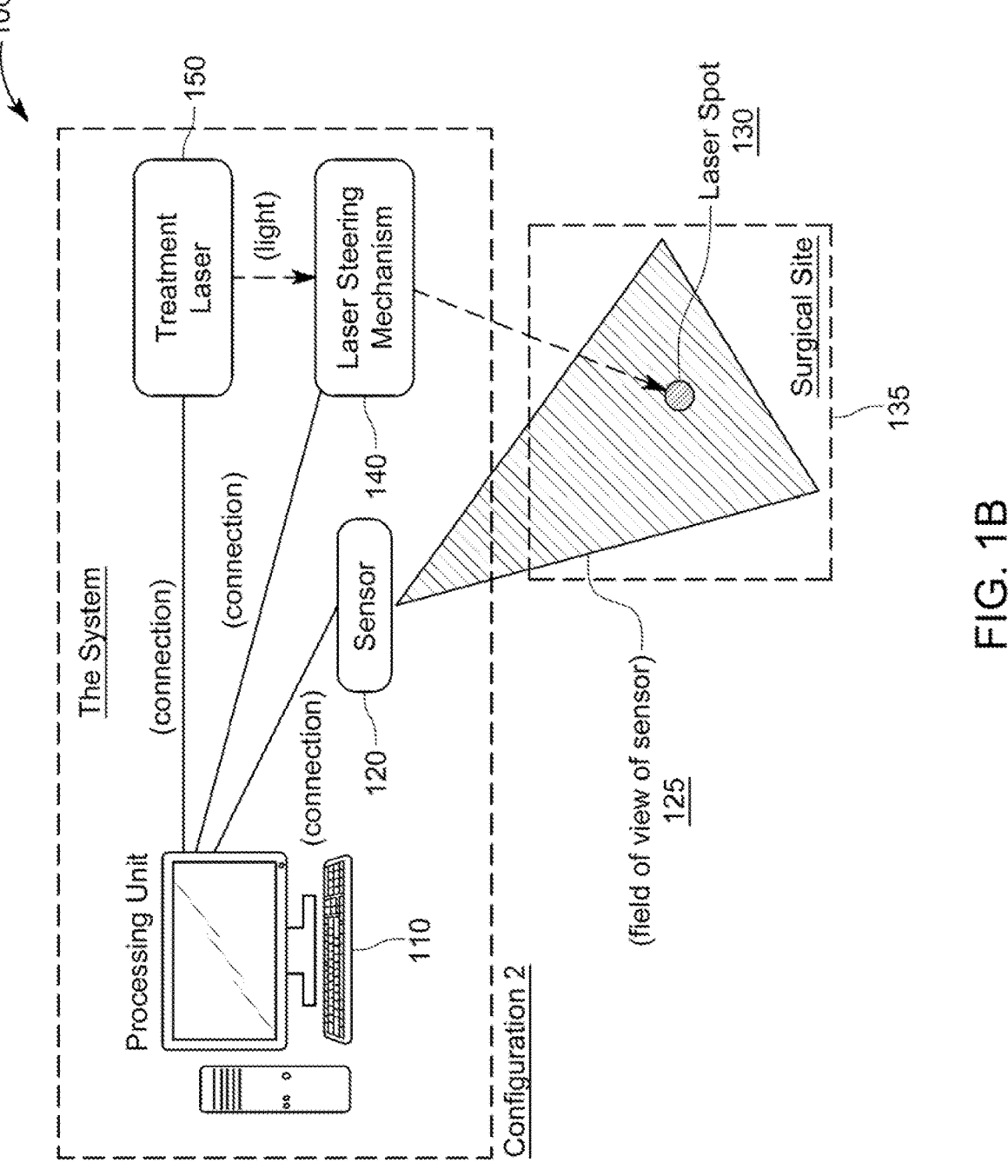
FIG. 1(B) depicts another block diagram of a laser treatment system in accordance with an illustrative embodiment of the present disclosure.

In FIG. 1(B), another embodiment of the laser treatment system 100 is illustrated. The components of the laser treatment system 100 are identical or substantially similar to the components of the laser treatment system 100 shown in FIG. 1(A). In FIG. 1(B), and unlike FIG. 1(A), the treatment laser 150 is part of the same system as the processing unit 110, sensor 120, and steering mechanism 140. In other words, the processing unit 110, sensor 120 and steering mechanism 140 are not accessories to the treatment laser 150 in FIG. 1(B). As in FIG. 1(A), the processing unit 110 will generate an optimal treatment path to enable the targeted therapy region to be provided, and alert the treatment laser 150 to provide the laser therapy to the targeted therapy region based on the optimal treatment path generated by the processing unit 110.

Figure 2A:
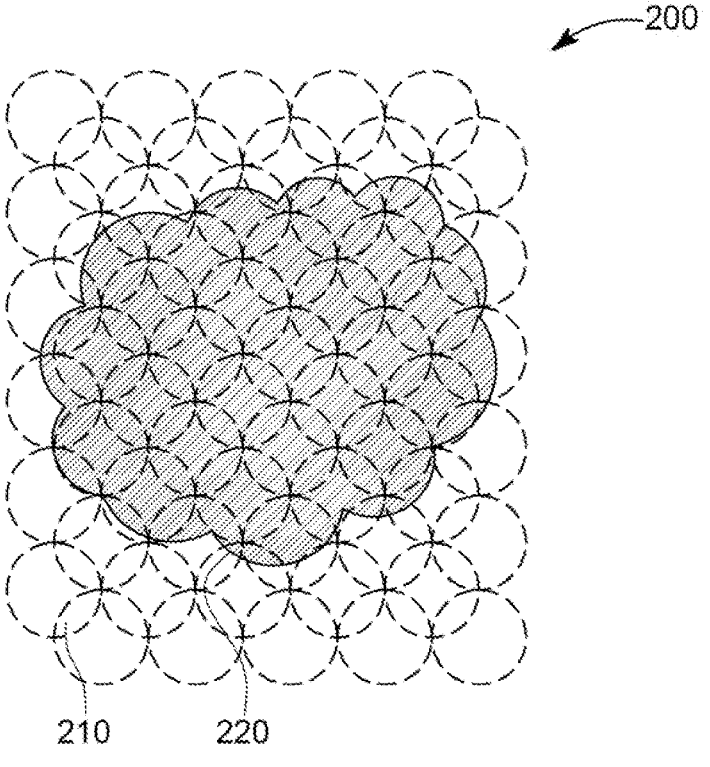
FIG. 2(A) illustrates laser treatment patterns in accordance with an illustrative embodiment of the present disclosure.
Figure 2B:
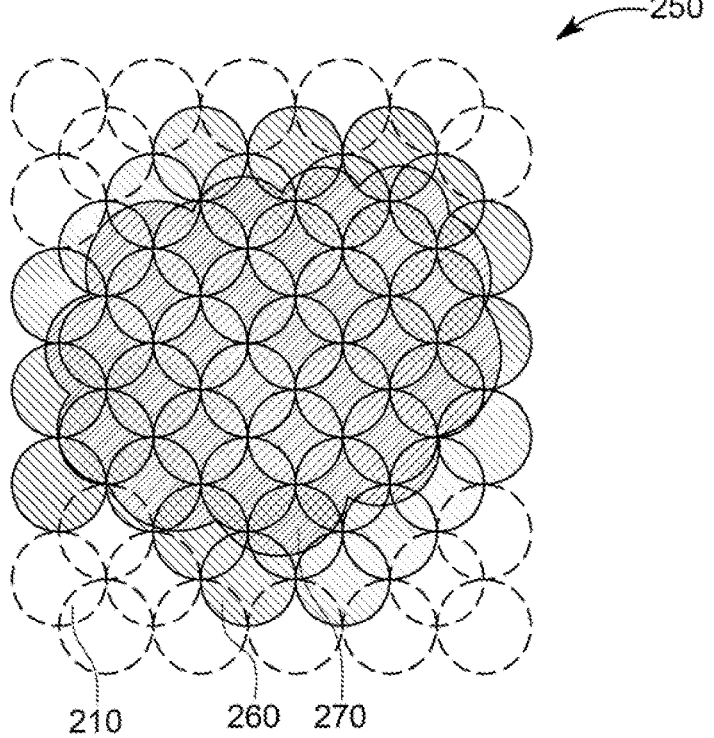
FIG. 2(B) depicts laser treatment patterns in accordance with an illustrative embodiment of the present disclosure.

Referring to FIGS. 2(A)-(B), a series of patterns (first, second, third, and final) of laser spot systems 200, 250 are illustrated in more detail. A targeted lesion 220 is also shown. The laser treatment system 100 is configured to detect and delineate the targeted lesion 220 or area within the surgical site 135. The laser treatment system 100 can create a targeted therapy region of the patient using the series of patterns produced by the treatment laser 150. The treatment laser 150 can produce the first pattern, second pattern, and third pattern. The final pattern can be used based on the first pattern, second pattern, and third pattern to define the targeted therapy region. Accordingly, with the first pattern, second pattern, third pattern, and final pattern, the targeted therapy region for the patient can be obtained. Uniform therapy can be delivered to a targeted therapy region while minimizing collateral damage to surrounding healthy skin and tissue.

In FIG. 2(A), in the laser spot system 200, the first pattern is derived from equal spacing of laser spots. The laser spots can be in the shape of rectangles, triangles, ellipses, ovoids, or any geometric shape to create desired treatment regions and energy density patterns as needed for the target therapy region. In an embodiment, a circular pattern or circular laser spot 210 is illustrated. As such, the first pattern is derived from equal spacing of the laser spots 210. Each laser spot 210 will be one diameter away from the adjacent laser spot 210. As such, the first pattern is derived from one diameter away for each laser spot 210, or the equal spacing of the center of each laser spot 210 from the adjacent laser spot 210. In other words, the treatment laser 150 will produce the first pattern of laser spots 210 in which each of the laser spots 210 are tangent to, or have coincident boundaries with, adjacent laser spots 210. Moreover, one diameter across the surface of the tissue will be described as the area of effect. The area of effect will correspond to the region of the laser beam of the treatment laser 150 with a fluency above the ablation threshold, although potentially corresponding to any energy delivery amount that is necessary for a desired effect. On such desired effect can be a photo-bleaching of a tattoo. Another desired effect can be the thermal necrosis or high temperature necrosis of a cutaneous (benign/malignant) lesion.

Still referring to FIG. 2(A), the second pattern is then created by duplicating the first pattern. The treatment laser 150 can duplicate the first pattern wherein the provided laser spots 210 are shifted in the lateral and longitudinal directions by a half a diameter or by some fraction of the diameter from the first pattern of laser spots 210. As such, the treatment laser 150 provides a second pattern of laser spots 210 that are shifted by a half diameter or by a fraction of one diameter (i.e., ⅓, ¼, etc.) in comparison to the first pattern of laser spots 210. As such, the second pattern of laser spots 210 are provided by the treatment laser 150 and are shifted by a certain fraction of a one diameter from the first pattern of laser spots 210.

In FIG. 2(A), as the treatment laser 150 has provided the first and second pattern of laser spots 210, a third pattern can be created. The third pattern can be created by merging the first and second pattern of laser spots 210 to form a continuous area. Moreover, the third pattern will ensure that the second pattern is overlapping with the first pattern, wherein each laser spot 210 of the second pattern is shifted by a fraction of a diameter in comparison to each laser spot 210 of the first pattern. The processing unit 110 can assist the treatment laser 150 to merge the first pattern and second pattern to enable the third pattern of laser spots 210 to be formed such that targeted lesion 220 within the tissue region of the patient is within the boundaries of the third pattern. The targeted lesion 220 can be tissue region within the patient that ultimately needs to receive the laser therapy. Moreover, the third pattern can enable the final pattern to be formed.

Referring to FIG. 2(B), the final pattern 270 is illustrated in the laser spot system 250. The final pattern 270 is created from the third pattern. Moreover, the final pattern 270 is created by removing the laser spots 210 from the treatment path 260 that are not fully contained within the targeted therapy region or targeted lesion 220. The targeted therapy region can be formed around the targeted lesion 220. The laser spots 210 within the treatment path 260 which do not overlap with the targeted lesion 220 or targeted therapy region can be removed to enable the final pattern 270 to be formed around the targeted therapy region. Once the final pattern 270 is formed, the processing unit 110 can assist the treatment laser 150 and provide either a positive or negative surgical margin wherein a desired amount of pathologic or non-pathologic tissue from the patient can be removed. With a positive surgical margin, the processing unit 110 will narrow the targeted therapy region 130. As a result, part of the targeted lesion 220 will not receive the laser therapy. Nevertheless, no part of the healthy tissue will receive the laser therapy. In contrast, with the negative surgical margin, the processing unit 110 will expand the targeted therapy region outside of the targeted lesion 220. Consequently, the targeted therapy region will include the targeted lesion 220 and also healthy skin and tissue. As such, healthy skin tissue will also receive laser therapy when the negative surgical margin is used.

In FIGS. 2(A)-(B), as needed or desired, laser properties such as the wavelength, spot size, shape, energy density, fluency, and energy profile can be varied such that the resulting final path for the laser therapy delivers the desired treatment to the targeted therapy region or targeted lesion 220. The choice of laser, and thus the wavelength, is dependent on the type of lesion as well as operator preference or availability, and the disclosed system can be used with many types of conventional or custom lasers. The targeted therapy region can vary spatially across the surface of the surgical site 135. One example can be where the laser treatment system 100 is providing laser therapy to a tattoo that exhibits varied ink concentrations across the surface of the tissue. In other words, more energy deposition would be required at darker regions of the tattoo. At lighter regions of the tattoo, less energy deposition would be required. Accordingly the final pattern 270 that is based off of the first pattern, second pattern, and third pattern, thereby encodes the desired effects of more or less energy deposition into the varied fluency levels at the proper locations. The treatment laser 150 will thereby be configured to provide the right amount of energy deposition at the various regions within the targeted therapy region or targeted lesion 220.

Figure 3A:
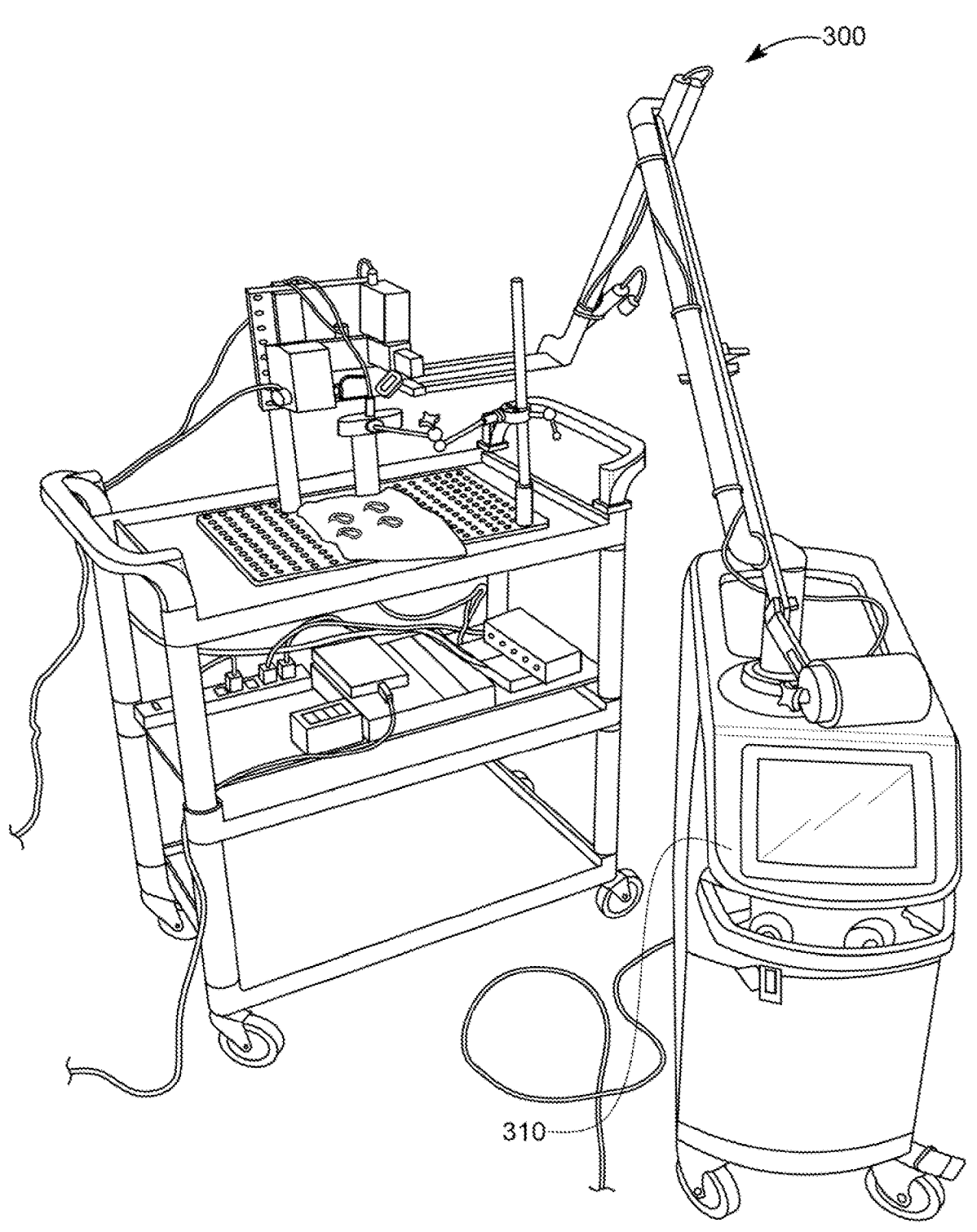
FIG. 3(A) a front view of a user interface for a laser treatment system in an illustrative embodiment of the disclosure.

FIG. 3(A) illustrates a front view of a laser treatment system 300. A treatment laser 310 is illustrated. The processing unit 110 can generate the optimal treatment path 260 to provide a plan to enable the targeted therapy region or targeted lesion 220 of the patent to receive laser therapy. As mentioned above, the first pattern includes laser spots 210 that are one diameter apart from the center of the adjacent laser spot 210 that are to be placed on the surface of the tissue. The second pattern is based off of the first pattern. The second pattern is shifted in the longitudinal and lateral directions from the first pattern by a fraction of a diameter of a laser spot 210 from the first pattern of laser spots 210. The second pattern will include laser spots 210 that are shifted by a fraction of a diameter in comparison to the laser spots 210 from the first pattern. In addition, the third pattern merges the first pattern and second pattern of laser spots 210 together. The final pattern 270 is then created from the third pattern. Moreover, the final pattern 270 is created by removing the laser spots 210 from the treatment path 260 not fully contained within the targeted therapy region or the targeted lesion 220.

In FIG. 3(A), as such, the final pattern 270 enables the optimal treatment path 260 around the targeted therapy region or targeted lesion 220 to be identified. The processing unit 110 can also define the targeted therapy region to leave a positive or negative surgical margin. The positive margin can involve the processing unit 110 narrowing the targeted therapy region. As such, a portion of the targeted lesion 220 will not be treated with laser therapy. However, no healthy tissue of the patient will be treated with the laser therapy. With the negative margin, the processing unit 110 will widen the targeted therapy region. As such, the targeted lesion 220 and also a portion of the healthy skin will receive the laser therapy. In either case, the processing unit 110 can widen or narrow the targeted therapy region for the patient as required.

Figure 3B:
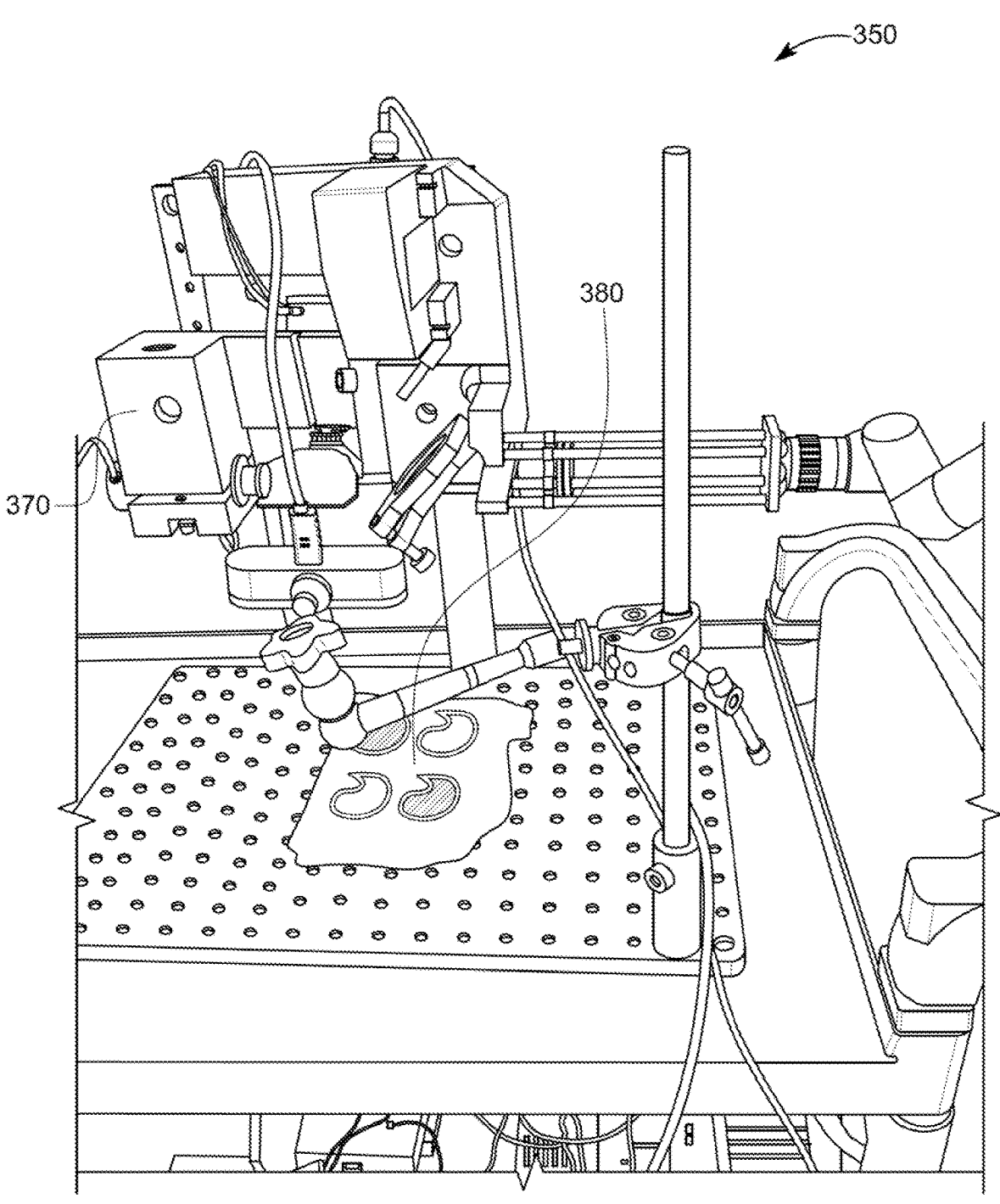
FIG. 3(B) depicts a front view of a steering mechanism of a laser treatment system in an illustrative embodiment of the disclosure.

With respect to FIG. 3(B), a steering mechanism 370 of a laser treatment system 350 is illustrated. Based on the optimal treatment path 260 that the processing unit 110 has generated, the steering mechanism 370 can move the treatment laser 310 to various positions around the surgical site 380. For ease of explanation, a sheet with tattoo ink is illustrated. Nevertheless, in other embodiments, human tissue will be part of the surgical site 380. As such, the steering mechanism 370 will move the treatment laser 310 to enable the treatment laser 310 to provide the first pattern of laser spots 210 according to the treatment path 260 that the processing unit 110 has generated. The steering mechanism 370 can also move the treatment laser 310 to the second pattern that is shifted by a predetermined fraction of the diameter of the laser spots 210 from the first pattern. Accordingly, after the steering mechanism 370 has moved the treatment laser 310 to the various positions based on the optimal treatment path 260 generated by the processing unit 110, the processing unit 110 can provide a command or alert the treatment laser 310 to prove laser therapy to the various positions to enable the final pattern 270 to be executed.

Figure 4:
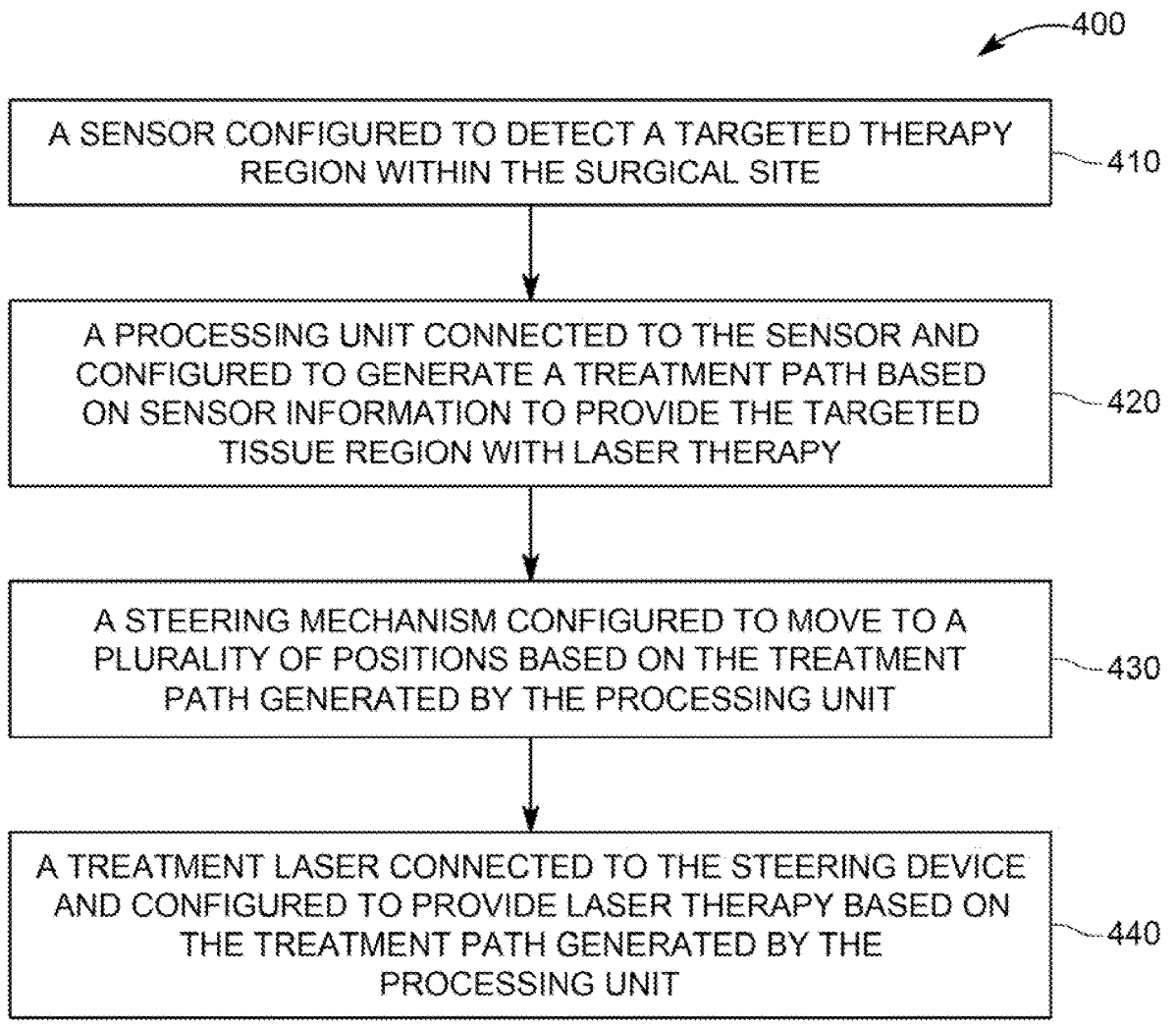
FIG. 4 depicts a flow chart in an illustrative embodiment of the disclosure.

In FIG. 4, a method 400 is illustrated in which the processing unit 110 generates an optimal treatment path 260 to enable laser therapy to be provided to a targeted therapy region. At step 410, a sensor 120 is configured in the laser treatment system 100. Sensor 120 can be, for example, a 3D depth-sensing camera, dual stereovision cameras, optical coherence tomography (OCT), a laser scanner, a laser distance sensor, or any other non-contact feedback modality. The sensor 120 can take an initial image of the surgical site 135 in which laser therapy is to be provided to a targeted therapy region. The sensor 120 can also take a final image of the surgical site 135 after the laser therapy has been provided to the targeted therapy region. The sensor 120 is configured to detect the targeted therapy region within the surgical site 135.

In FIG. 4, at step 420, the processing unit 110 is connected to the sensor 120. The processing unit 110 can be found, for example, within the computing device shown in FIGS. 1(A) and 1(B). The processing unit 110 is configured to generate a treatment path 260 based on information provided by the sensor 120 to provide a targeted tissue region with laser therapy. The treatment path 260 includes the generating a first pattern of laser spots 210 one diameter apart. The treatment path 260 also includes generating a second pattern of laser spots 210 that are shifted in the latitudinal and longitudinal direction from the first pattern of laser spots 210. The treatment path 260 will also include a third pattern that merges the first pattern and the second pattern of laser spots 210. Further, the treatment path 260 generated by the processing unit 110 will also include a final pattern 270 created from the third pattern in which the laser spots 210 of the treatment path 260 which are outside of the targeted lesion 220 are removed.

In FIG. 4, at step 430, a steering mechanism 140 is connected to the processing unit 110. The steering mechanism 140 is configured to move the treatment laser 150 to various positions based on the treatment path 260 generated by the processing unit 110. The processing unit 110 alerts or commands the treatment laser 150 to produce the laser spots 210 based on the generated treatment path 260. Further, the treatment laser 150 is alerted to remove the laser spots 210 from the treatment path 260 that are not fully contained within the targeted lesion 220.

In FIG. 4, at step 440, the treatment laser is configured to receive an alert or command from the processing unit 110 to provide the laser therapy to the various regions and the targeted lesion 220 or targeted therapy region. As the steering mechanism 140 has moved the treatment laser 150 to the various positions to enable the targeted therapy region to be established, the processing unit 110 will alert the treatment laser 150 to provide the laser therapy to the targeted therapy region. In one or more embodiments, the processing unit 110 can adjust the targeted therapy region to have a positive or negative surgical margin. With the positive surgical margin, the processing unit 110 narrows the targeted therapy region, and a portion of the targeted lesion 220 is left untreated. In contrast, with the negative surgical margin, the processing unit 110 expands the targeted therapy region. As a result, a portion of healthy tissue is treated with laser therapy in addition to the targeted lesion 220.

Figure 5:
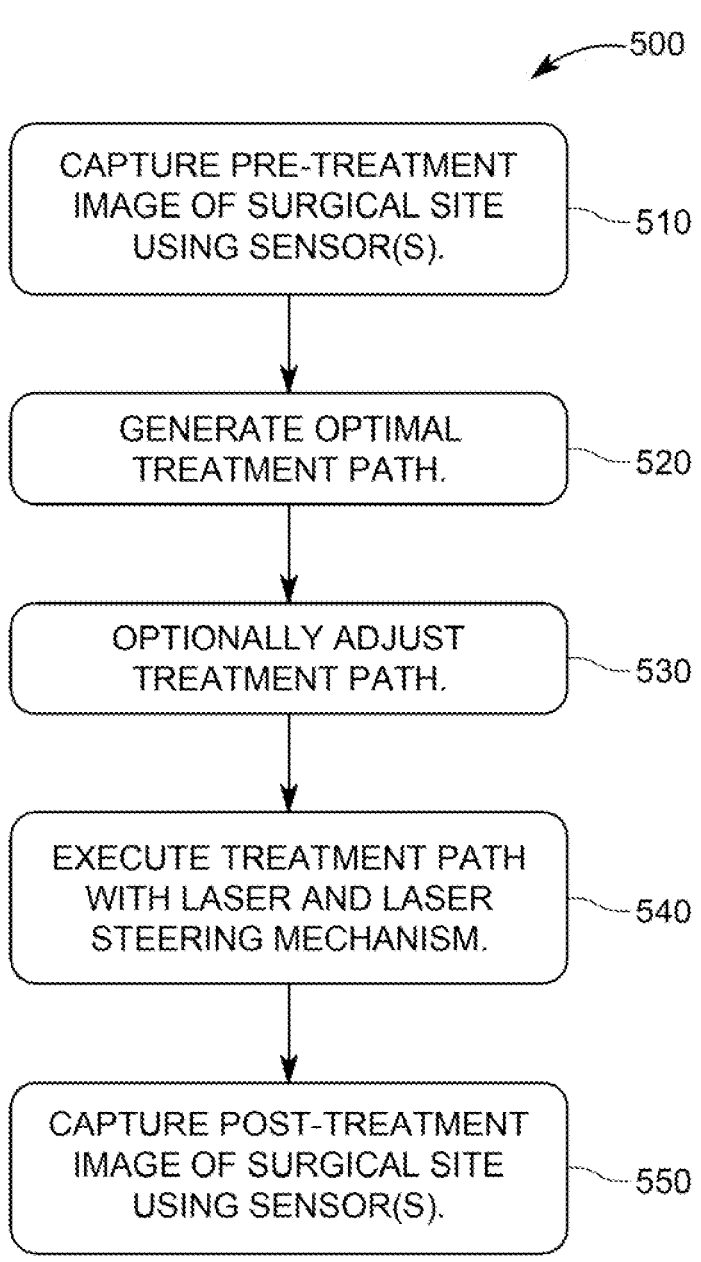
FIG. 5 shows another flow chart in an illustrative embodiment of the disclosure.

In FIG. 5, another illustration of a method 500 of the laser treatment system is illustrated. At step 510, the sensor 120 captures a pre-treatment image of the surgical site 135. The sensor 120 can include a depth camera and/or a color camera. The sensor 120 having a depth camera and/or a color camera can generate an effective and clear pre-treatment image of the surgical site 135. The surgical site 135 can include the tissue region of the patient with the targeted lesion 220.

Referring to FIG. 5, at step 520, the processing unit 110 generates the optimal treatment path 260 to ultimately enable laser therapy to be provided to the targeted therapy region or targeted lesion 220. The optimal treatment path 260 includes a final pattern 270 determined by the steps described hereinabove.

In FIG. 5, at step 530, the processing unit 110 can optionally adjust the treatment path 260. The processing unit 110 can adjust the targeted therapy region to have a positive or negative surgical margin. With a positive surgical margin, the processing unit 110 will narrow the targeted therapy region so that a portion of the targeted lesion 220 is untreated. With the negative surgical margin, the processing unit 110 will widen the targeted therapy region to where a portion of healthy tissue in addition to the targeted lesion 220 will be treated with laser therapy. As such, the processing unit 110 can optionally have the treatment path 260 to have a positive or negative surgical margin with the targeted therapy region.

In FIG. 5, at step 540, the treatment path 260 is executed using the steering mechanism 140 and the treatment laser 150. The steering mechanism 140 will move the treatment laser 150 to various positions based on the treatment path 260 generated by the processing unit 110. In other words, the steering mechanism 140 will move the treatment laser 150 to the various positions and the treatment laser 150 will provide the laser spots 210 based on the treatment path 260. Further, the treatment laser 150 will remove the laser spots 210 that are not fully contained within the targeted lesion 220.

In FIG. 5, at step 550, a post-treatment image of the surgical site 135 is captured. The sensor 120 (i.e., a depth camera and/or color camera) will capture an image of the post surgical site 135 after laser therapy has been applied to the targeted therapy region. The sensor 120 will capture the image of the surgical site 135 that includes the targeted therapy region that has received laser therapy from the treatment laser 150.

In summary, the laser treatment system 100 can provide laser therapy to the targeted therapy region based on the optimal treatment path 260 generated by the processing unit 110 configured within the computing device. The processing unit 110 will generate the optimal treatment path 260 based on a first and second pattern of laser spots 210. A third pattern will merge the first and second pattern. The final pattern 270 of the optimal treatment path 260 will remove the laser spots 210 from the treatment path 260 that do not fully overlap with the targeted lesion 220 or targeted therapy region. The processing unit 110 can also adjust the targeted therapy region to have a positive or negative surgical margin. As described above, the positive surgical margin will narrow the targeted therapy region, and omit a portion of the targeted lesion 220 from receiving laser therapy. With the negative surgical margin, the processing unit 110 widens the targeted therapy region to where a portion of healthy tissue will receive laser therapy in addition to the targeted lesion 220.

Further, the steering mechanism 140 will move the treatment laser 150 to the various positions to provide the first and second pattern of laser spots 210, and to remove the non-overlapping laser spots 210 that do not overlap with the targeted lesion 220 to enable the final pattern 270 to be established. After the optimal treatment path 260 has been executed, the processing unit 110 will alert or provide a command to the treatment laser 150 to provide laser therapy to the targeted lesion 220 or targeted therapy region. Overall, the targeted lesion 220 is treated with laser therapy according to the optimal treatment path 260 generated by the processing unit 110. Further, damage to healthy tissue surrounding the targeted lesion 220 is minimized.

The present disclosure is applicable to a variety of human and animal procedures in which the tissue is treated via removal, debridement, cauterization, thermal necrosis, photobleaching, or otherwise changed or manipulated using the disclosed systems and methods. Moreover, since the majority of the components are away from the surgical site 135 and connected via cables and optical fibers, the distal end of the device can be small, such as on the order of 6 cubic inches.

The operator uses a user interface that can be implemented on a touch-screen that allows for user input via a standard keyboard, standard mouse, using their finger-tips, or using a stylus with a precision tip. The operator can set the laser parameters on the conventional laser system but can control the laser positioning using the disclosed user interface. The operator can "draw" a boundary on an image of the surgical site 135 indicating the region for treatment.

It is to be understood that the disclosure teaches just some examples of embodiments in accordance with the present disclosure and that many variations of the disclosure can easily be devised by those skilled in the art after reading this disclosure and that the scope of the present disclosure is to be determined by the following claims.

What is claimed is:

1. A laser treatment system, comprising:
   one or more sensors to obtain one or more images of a tissue surface;
   a processing unit, connected to the one or more sensors, to:
   determine a first pattern of non-overlapping laser spots,
   determine a second pattern of non-overlapping laser spots, wherein each laser spot of the second pattern overlaps at least one laser spot of the first pattern,
   determine a third pattern of overlapping laser spots that is an overlay of the first pattern and the second pattern, wherein each laser spot of the third pattern overlaps at least one other laser spot of the third pattern, and
   establish, based on the one or more images of the tissue surface, a targeted therapy region to receive laser therapy, the targeted therapy region containing a plurality of the laser spots of the third pattern;
   a steering device to receive one or more signals from the processing unit to move to a plurality of positions around the tissue surface, the plurality of positions corresponding to the plurality of laser spots of the third pattern within the targeted therapy region; and
   a treatment laser connected to the steering device, to provide the laser therapy to the targeted therapy region from the plurality of positions.

2. The laser treatment system of claim 1, wherein the one or more sensors comprises at least one of a three-dimensional depth sensing camera, a laser scanner camera, a laser distance sensor, or dual stereovision cameras.

3. The laser treatment system of claim 1, wherein each laser spot of the first pattern is tangent to at least one other laser spot of the first pattern, and wherein each laser spot of the second pattern is tangent to at least one other laser spot of the second pattern.

4. The laser treatment system of claim 1, wherein the establishing of the targeted therapy region results in a negative surgical margin.

5. The laser treatment system of claim 1, wherein the establishing of the targeted therapy region results in a positive surgical margin.

6. The laser treatment system of claim 1, wherein the treatment laser illuminates a first laser spot of the third pattern with a first energy density and a second laser spot of the third pattern with a second energy density that is different than the first energy density.

7. The laser treatment system of claim 1, wherein the treatment laser illuminates a first laser spot of the third pattern with a first wavelength and a second laser spot of the third pattern with a second wavelength that is different than the first wavelength.

8. The laser treatment system of claim 1, wherein the treatment laser illuminates a first laser spot of the third pattern with a first laser spot size and a second laser spot of the third pattern with a second laser spot size that is different than the first laser spot size.

9. The laser treatment system of claim 1, wherein the treatment laser illuminates a first laser spot of the third pattern with a first laser spot shape and a second laser spot of the third pattern with a second laser spot shape that is different than the first laser spot shape.

10. The laser treatment system of claim 1, wherein the laser therapy treats the targeted therapy region via at least one of thermal necrosis, debridement, cauterization, photo-bleaching, or tissue removal.

11. A method comprising:

obtaining, by one or more sensors, one or more images of a tissue surface;

determining a first pattern of non-overlapping laser spots;

determining a second pattern of non-overlapping laser spots, wherein each laser spot of the second pattern overlaps at least one laser spot of the first pattern;

determining a third pattern of overlapping laser spots that is an overlay of the first pattern and the second pattern, wherein each laser spot of the third pattern overlaps at least one other laser spot of the third pattern;

establishing by a processing unit, based on the one or more images of the tissue surface, a targeted therapy region to receive laser therapy, the targeted therapy region containing a plurality of the laser spots of the third pattern; and illuminating, by a treatment laser, the plurality of laser spots of the third pattern to provide the laser therapy to the targeted therapy region.

12. The method of claim 11, wherein the one or more sensors comprises at least one of a three-dimensional depth sensing camera, a laser scanner camera, a laser distance sensor, or dual stereovision cameras.

13. The method of claim 11, wherein each laser spot of the first pattern is tangent to at least one other laser spot of the first pattern, and wherein each laser spot of the second pattern is tangent to at least one other laser spot of the second pattern.

14. The method of claim 11, wherein the establishing of the targeted therapy region results in a negative surgical margin.

15. The method of claim 11, wherein the establishing of the targeted therapy region results in a positive surgical margin.

16. The method of claim 11, wherein the treatment laser illuminates a first laser spot of the third pattern with a first energy density and a second laser spot of the third pattern with a second energy density that is different than the first energy density.

17. The method of claim 11, wherein the treatment laser illuminates a first laser spot of the third pattern with a first wavelength and a second laser spot of the third pattern with a second wavelength that is different than the first wavelength.

18. The method of claim 11, wherein the treatment laser illuminates a first laser spot of the third pattern with a first laser spot size and a second laser spot of the third pattern with a second laser spot size that is different than the first laser spot size.

19. The method of claim 11, wherein the treatment laser illuminates a first laser spot of the third pattern with a first laser spot shape and a second laser spot of the third pattern with a second laser spot shape that is different than the first laser spot shape.

20. The method of claim 11, wherein the laser therapy treats the targeted therapy region via at least one of thermal necrosis, debridement, cauterization, photobleaching, or tissue removal.

* * * * *